(12) United States Patent
Durniak et al.

(10) Patent No.: US 9,156,033 B2
(45) Date of Patent: Oct. 13, 2015

(54) LAB ON A CHIP

(71) Applicant: INTERNATIONAL BUSINESS MACHINES CORPORATION, Armonk, NY (US)

(72) Inventors: Timothy Durniak, Poughkeepsie, NY (US); Robert R. Friedlander, Southbury, CT (US); James R. Kraemer, Albuquerque, NM (US)

(73) Assignee: International Business Machines Corporation, Armonk, NY (US)

( * ) Notice: Subject to any disclaimer, the term of this patent is extended or adjusted under 35 U.S.C. 154(b) by 287 days.

(21) Appl. No.: 13/929,111

(22) Filed: Jun. 27, 2013

(65) Prior Publication Data

US 2013/0287632 A1  Oct. 31, 2013

Related U.S. Application Data

(63) Continuation of application No. 13/051,605, filed on Mar. 18, 2011, now abandoned.

(51) Int. Cl.
| | |
|---|---|
| *G01N 21/00* | (2006.01) |
| *B01L 3/00* | (2006.01) |
| *G01N 15/10* | (2006.01) |
| *G01N 15/14* | (2006.01) |
| *G01N 1/28* | (2006.01) |

(Continued)

(52) U.S. Cl.
CPC ....... *B01L 3/502715* (2013.01); *B01L 3/50273* (2013.01); *F04B 19/006* (2013.01); *G01N 1/28* (2013.01); *G01N 15/1056* (2013.01); *G01N 15/1436* (2013.01); *G01N 15/1459* (2013.01); *G01N 21/75* (2013.01); *B01L 2200/10* (2013.01); *B01L 2300/0654* (2013.01); *B01L 2300/0867* (2013.01); *B01L 2300/1861* (2013.01); *B01L 2400/0442* (2013.01); *B01L 2400/0481* (2013.01); *B01L 2400/0677* (2013.01)

(58) Field of Classification Search
None
See application file for complete search history.

(56) References Cited

U.S. PATENT DOCUMENTS

| | | | |
|---|---|---|---|
| 4,865,813 | A | 9/1989 | Leon |
| 6,150,102 | A | 11/2000 | Mills et al. |
| 6,690,049 | B2 | 2/2004 | Suzuki et al. |

(Continued)

FOREIGN PATENT DOCUMENTS

| | | |
|---|---|---|
| CN | 101806723 A | 8/2010 |
| DE | 10 2008 060 332 A1 | 6/2010 |

(Continued)

OTHER PUBLICATIONS

S. Berry et al., "New Methods to Transport Fluids in Micro-Sized Devices", MIT, Lincoln Laboratory Journal, vol. 17, No. 2, 2008, pp. 1-11.

(Continued)

*Primary Examiner* — Robert Xu
(74) *Attorney, Agent, or Firm* — John R. Pivnichny; Law Office of Jim Boice

(57) ABSTRACT

A Lab On a Chip (LOC) has a Sample Preparation Module (SPM) coupled to a sample inlet, a microchannel coupled to the SPM, and an optic module optically proximate to the microchannel. The optic module holds multiple lenses, each of which has a different effective focal length, such that all fields of focus within the microchannel are covered as objects suspended within the liquid sample pass through the microchannel.

10 Claims, 8 Drawing Sheets

(51) Int. Cl.
  *G01N 21/75* (2006.01)
  *F04B 19/00* (2006.01)

(56) References Cited

U.S. PATENT DOCUMENTS

| | | |
|---|---|---|
| 7,291,497 B2 | 11/2007 | Holmes et al. |
| 7,659,977 B2 | 2/2010 | Koo |
| 7,727,723 B2 | 6/2010 | Pollack et al. |
| 7,756,559 B2 | 7/2010 | Abreu |
| 7,851,251 B2 | 12/2010 | Tseng et al. |
| 8,107,693 B2 | 1/2012 | Osborne et al. |
| 8,263,386 B2 | 9/2012 | Yoo |
| 8,464,076 B2 | 6/2013 | Durniak et al. |
| 2003/0118184 A1 | 6/2003 | Kim |
| 2005/0270611 A1 | 12/2005 | Oshiro et al. |
| 2008/0170299 A1 | 7/2008 | Kawabata |
| 2008/0258086 A1 | 10/2008 | Mathewson et al. |
| 2009/0061418 A1 | 3/2009 | Kriz et al. |
| 2009/0322869 A1 | 12/2009 | Peng |
| 2010/0200781 A1 | 8/2010 | Khorasani et al. |
| 2012/0238032 A1 | 9/2012 | Durniak et al. |
| 2012/0246488 A1 | 9/2012 | Durniak et al. |
| 2013/0227305 A1 | 8/2013 | Durniak, et al. |
| 2013/0286195 A1 | 10/2013 | Durniak, et al. |

FOREIGN PATENT DOCUMENTS

| | | |
|---|---|---|
| JP | 2008172682 | 7/2008 |
| JP | 2010171450 | 8/2010 |
| JP | 2010245129 | 10/2010 |
| WO | 2005108963 A1 | 11/2005 |

OTHER PUBLICATIONS

J. Cho et al., "Cerenkov Radiation Imaging As a Method for Quantitative Measurements of Beta Particles in a Microfluidic Chip", IOP Publishing, Physics in Medicine and Biology, Phys. Med. Biol. 54, Oct. 21, 2009, pp. 6757-6771.

T. Liu et al. "Photoelectric Automatic Focusing System Based on Interference", Optics and Lasers in Engineering, vol. 36, No. 4, 345-353, Oct. 2001 (Abstract).

S. Moon et al., "Integrating Microfluidics and Lensless Imaging for Point-of-Care Testing", Biosens Bioelectron, Jul. 15, 2009, pp. 3208-3214.

R. Daw et al., "Insight: Lab on a Chip", Nature International Weekly Journal of Science, Supplements, vol. 442, No. 7101, pp. 367-418.

U.S. Appl. No. 13/051,605—Election/Restriction Office Action Mailed Jan. 2, 2013.

International Application No. PCT/CA2012/050169—International Search Report and Written Opinion, Jul. 13, 2012.

U.S. Appl. No. 13/051,605—Non-Final Office Action Mailed Feb. 5, 2013.

Liu, Y. et al., "Enhancing Lab-On-A-Chip Performance Via Tunable Parallel Liquid Microlens Arrays," 2009, Proc of SPIE, vol. 7167, pp. 71670L-1-71670L-10.

Hellman, A. N. et al., "Laser-Induced Mixing in Microfluidic Channels," 2007, Analytical Chemistry, vol. 79(12), pp. 4484-4492.

Wang, G. R. et al., "A Laser Induced Cavitation Pump," 2004, Journal of Micromechanics and Microengineering, vol. 14, pp. 1037-1046.

U.S. Appl. No. 13/071,262—Election/Restriction Office Action Mailed Dec. 18, 2012.

U.S. Appl. No. 13/071,262—Notice of Allowance Mailed Feb. 1, 2013.

U.S. Appl. No. 13/929,332—Non-Final Office Action Mailed Mar. 6, 2014.

LAB ON A CHIP

The present application is a continuation of U.S. patent application Ser. No. 13/051,605, filed on Mar. 18, 2011, and entitled, "Lab on a Chip," which is incorporated herein by reference.

BACKGROUND

The present disclosure relates to the field of integrated circuits, and specifically to the use of integrated circuits in examining fluid samples. Still more particularly, the present disclosure relates to the use of integrated circuits to capture images of components of a fluid sample.

Laboratory tests on a single chip have developed rapidly in the last decade. The advantages of using a minimal amount of fluids to be tested, the speed of a chip to complete the tests, the minuscule (nanogram, picogram, femtogram) quantity of reagents necessary for reaction, and the ability to build these devices in silicon chip fabrication facilities has led to rapid scientific and economic expansion of the field. However, most Lab On a Chip (LOC) devices are relatively complex compared to their capacity. More specifically, most LOC devices have limited optical capabilities and require complex preparation before use when compared to their capabilities.

SUMMARY

In one embodiment of the present disclosure, a Lab On a Chip (LOC) comprises a sample inlet for receiving a liquid sample. The LOC also comprises a Sample Preparation Module (SPM) coupled to the sample inlet, a microchannel coupled to the SPM, and an optic module optically proximate to the microchannel. The optic module holds multiple lenses, each of which has a different effective focal length, such that all fields of focus within the microchannel are covered as objects suspended within the liquid sample pass through the microchannel.

In one embodiment, a method and/or computer program product analyzes a test sample on a Lab On a Chip (LOC). A sample preparation module in the LOC receives a fluid sample, from which a prepared fluid sample is created. The prepared fluid sample, which includes multiple suspended objects, passes through a microchannel that is situated between a light source and a lens chamber in the LOC. The lens chamber holds multiple lenses, each of which has a different effective fixed focal length. An optic image of each of the multiple suspended objects is created and converted into a digital image.

DETAILED DESCRIPTION

Figure 1:
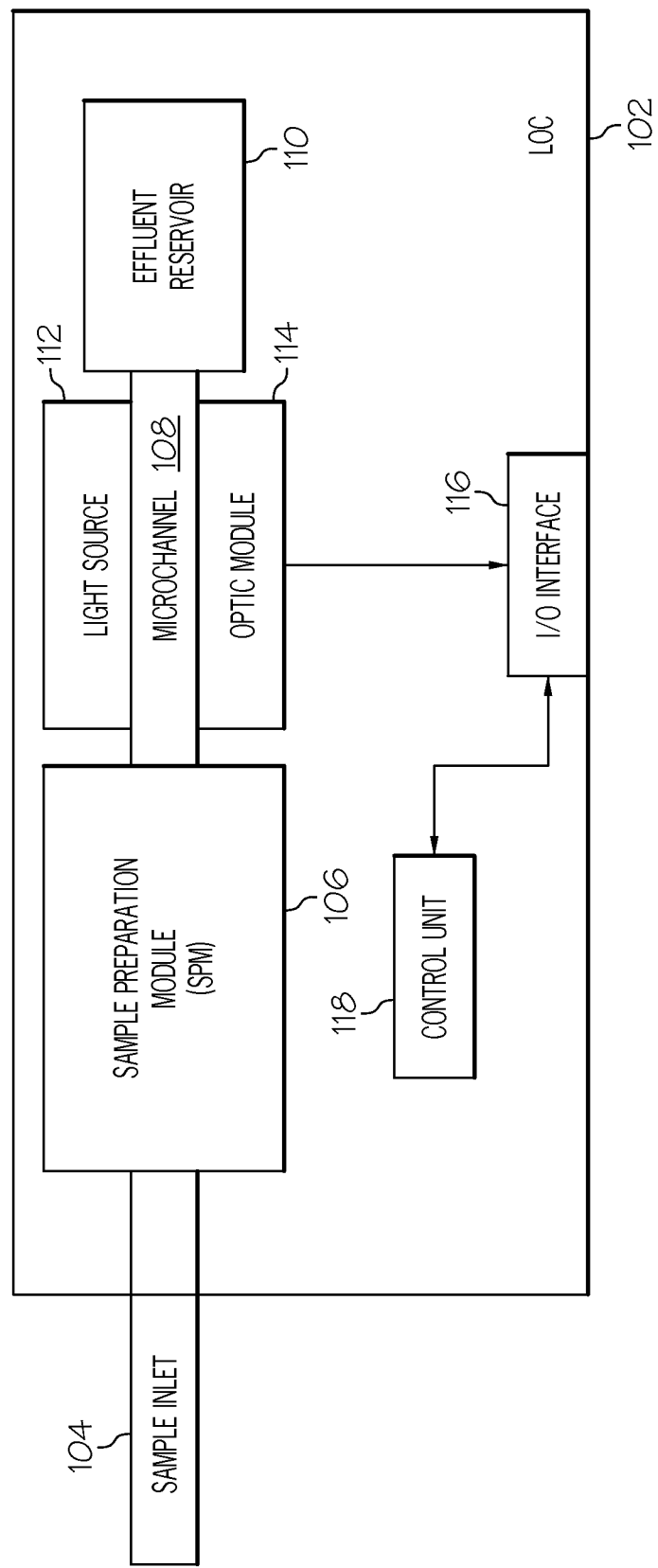
FIG. 1 depicts an exemplary simple Lab On a Chip (LOC) as contemplated in one embodiment of the present disclosure.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

With reference now to the figures, and in particular to FIG. 1, an exemplary Lab On a Chip (LOC) 102 as contemplated by the present disclosure is presented. LOC 102 is an on-chip device that, in one embodiment, is pre-packaged with some or all of the components depicted in FIGS. 1-6 and 8. LOC 102 may be powered by an internal power supply (e.g., a battery—not shown) or an external power supply (e.g., via a power port—also not shown). Regardless of how LOC 102 is powered, it is capable of autonomously, or in conjunction with ancillary logic such as a coupled computer/server, optically analyzing a material sample. That is, LOC 102, as described herein, is capable of capturing visual images of objects that are suspended in a liquid sample, such as a medical serum sample, a whole blood sample, a chemical process sample, a water sample, etc. These suspended objects may be blood cells, parasites, metallic particles, or any other material that is capable of being photographed using the components, or their equivalent, described herein.

As depicted in FIG. 1, the fluid/liquid sample is inserted into a sample inlet 104 by injection, capillary action, gravity, etc. The sample contains both a transport medium (e.g., serum) as well as objects (e.g., red blood cells) to be examined/visualized. In one embodiment, the sample must be prepared before being visually examined. This preparation may include the introduction of dyes, catalysts, coagulators, etc. (referred to as "reagents" in the present disclosure) into the sample in order to make the objects within the fluid more conducive to being photographed and/or visually inspected. As described in further detail below, this preparation is performed in a Sample Preparation Module (SPM) 106.

Once the sample has been prepared with SPM 106, it passes through a microchannel 108, and is then preferably discarded into an internal effluent reservoir 110, in order to avoid contaminating the user of the LOC with the prepared sample. Alternatively, the sample can simply pass through the LOC 102 and out a process sample outlet (not shown), assuming that the sample, processed or unprocessed, is either not harmful to persons or the environment, or else is properly disposed of.

While passing through the microchannel 108, the sample is illuminated by a light source 112, which may be a set of Light Emitting Diodes (LEDs), luminescent material, natural ambient light, etc. If the light source 112 is a luminescent material, then it can be activated by mechanically mixing one or more materials together, energizing (e.g., hitting with a certain frequency of electromagnetic energy) a photoluminescent material, etc. Any variation of the light source 112 described herein can be under the control of a control unit 118.

As light from the light source 112 illuminates the sample within the microchannel 108, images of objects within the sample are captured/generated/processed by an optic module 114 (described in exemplary details below). The optic module 114 is optically proximate to the microchannel 108, meaning that light from the microchannel 108 is capable of being received by the optic module 114. The images of objects within the microchannel 108 are the result of light passing through or reflecting off one or more objects suspended within the fluid in the microchannel. Captured/generated/processed images of the objects are then passed to an Input/Output (I/O) interface 116, which may be coupled to a data port, external monitor, an external computer/server, etc. (none of which are depicted). I/O interface 116 also allows for commands to be sent to and feedback received from a control unit 118, which controls the operations of the SPM 106, light source 112, and optic module 114.

Figure 2:
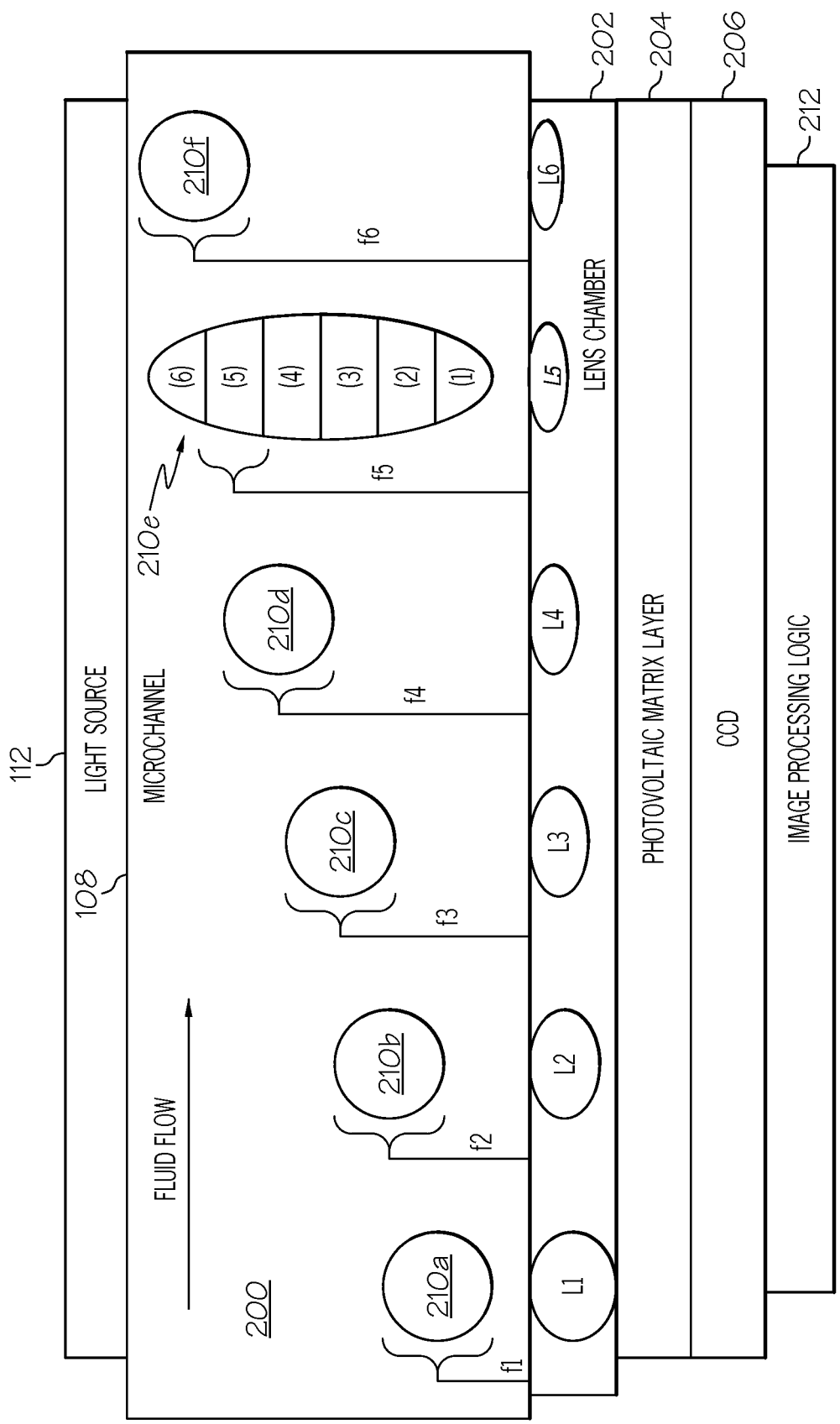
FIG. 2 illustrates additional detail of one embodiment of an optic module depicted in FIG. 1.

With reference now to FIG. 2, additional detail of the optic module 114 is presented in one exemplary embodiment as elements 202, 204, 206 and 212. That is, in one embodiment of the present disclosure, the optic module 114 shown in FIG. 1 comprises a lens chamber 202, a photovoltaic matrix layer 204, a Charge-Coupled Device (CCD) 206, and an image processing logic 212.

As depicted, lens chamber 202 contains multiple lenses L1-L6. While only six lenses are depicted within lens chamber 202, it is understood that the actual number of lenses may be as few as 2 or as many as deemed necessary by the designer. Each of the lenses L1-L6 has a different focal length, depicted as corresponding focal lengths f1-f6, which describe the distance from the lenses to areas within the microchannel 108 where objects will be in clear focus (i.e., crisp and not blurred). These areas within the microchannel 108 are referred to as strata, with each strata having a different depth of field (or field of focus) associated with a corresponding lens.

For explanatory purposes, assume that a liquid sample 200 is flowing through microchannel 108, and that objects 210a-f are suspended within the liquid sample 200. As described above, each of the lenses L1-L6 has a different focal length (and thus a different depth of field). These different focal lengths ensure that at least one of the lenses L1-L6 will be able to focus/create a crisp image of each of the objects 210a-f, depending on the strata (i.e., position within the microchannel relative to the lenses L1-L6) in which each of the objects 210a-f is located as it flows through the microchannel.

For example, lens L1 has a focal length of f1. This means that lens L1 is able to focus in on an object (e.g., object 210a) that is physically located near the distance f1 from lens L1. Thus, light is transmitted from light source 112 and traverses through object 210a, and is then focused by lens L1 to create an optic image of object 210a that is crisp and clear (in focus). However, lens L2 is unable to create a clearly focused image of object 210a, since the focal length f2 does not include the depth of field in which object 210a is situated as is moves through the microchannel 108 at a given strata. Nonetheless, lens L2 is able to create a crisp image of object 210b, which is within the depth of field f2 of lens L2. In the example shown in FIG. 2, lens L1 is able to focus the image of object 210a, lens L2 is able to focus the image of object 210b, lens L3 is able to focus the image of object 210c, lens L4 is able to focus the image of object 210d, and lens L6 is able to focus the image of object 210f. Note that object 210e is too large to fit within the depth of field of any single lens from lenses L1-L6. In order to create a focused image of all of object 210e, "snapshots" of object 210e are taken by using each of the lenses L1-L6 as object 210e passes by. These snapshots result in six images (1)-(6) being created with the use of respective lenses L1-L6. These six images are then combined to create a composite focused image of object 210e.

As stated above, the lenses L1-L6 focus the light from light source 112 that has traversed through (or reflected off) the objects 210a-f in order to create focused visual images of the objects 210a-f. These focused light images pass through to a photovoltaic matrix layer 204, which contains material that converts the light energy from the focused light images into electrical energy of comparable levels. That is, the focused light image is made up of varying hues and intensities of light. These varying hues/intensities are quantified by the photovoltaic matrix layer 204 as corresponding levels of electrical energy, which are then passed on to a Charge-Coupled Device (CCD) 206. CCD 206 moves these electrical charges to an image processing logic 212, where the charges are manipulated into a digital value. The CCD 206 moves the electrical charges by "shifting" the charges between stages within the CCD 206, one at a time, into the image processing logic 212. More specifically, CCD 206 shifts charges between capacitive "bins" within CCD 206 in order to transfer charges between bins. Thus, a CCD can be thought of as a "shift register" in which charges, rather than simple ones and zeros, from bins are shifted across a matrix. Together, the lens chamber 202, the photovoltaic matrix layer 204, the CCD 206, and the image processing logic 212 make up an image processing component of the optic module 114.

The control unit 118 depicted in FIG. 1 controls the timing at which images are captured by the optic module 114. In one embodiment, this timing is performed by measuring (or controlling) the flow rate of the liquid sample 200 through the microchannel 108. This timing 1) ensures that each of the objects 210a-f will be in focus at some point in time as it passes over the lenses L1-L6, and in the case of a counter mechanism being part of the control unit 118, can be used to 2) avoid counting a same object twice. Assuming that the suspended objects 210a-f travel at the same rate as the transport medium of the liquid sample 200, then the control unit 118 is able to 1) time the capture of the images generated by the optic module 114 such that every object will be photographed in focus, and to 2) determine that object 210a, which was captured in focus by lens L1 and counted as it passed over lens L1, is the same object 210a that is out of focus in the image captured by lens L2, and thus should not be recounted.

Note that the different focal lengths f1-f6 may be the result of different physical shapes of their corresponding lenses L1-L6, as depicted. In one embodiment, these different focal lengths f1-f6 are the result of different light refracting properties of the different lenses L1-L6, which may actually have the same physical shapes.

Figure 3:
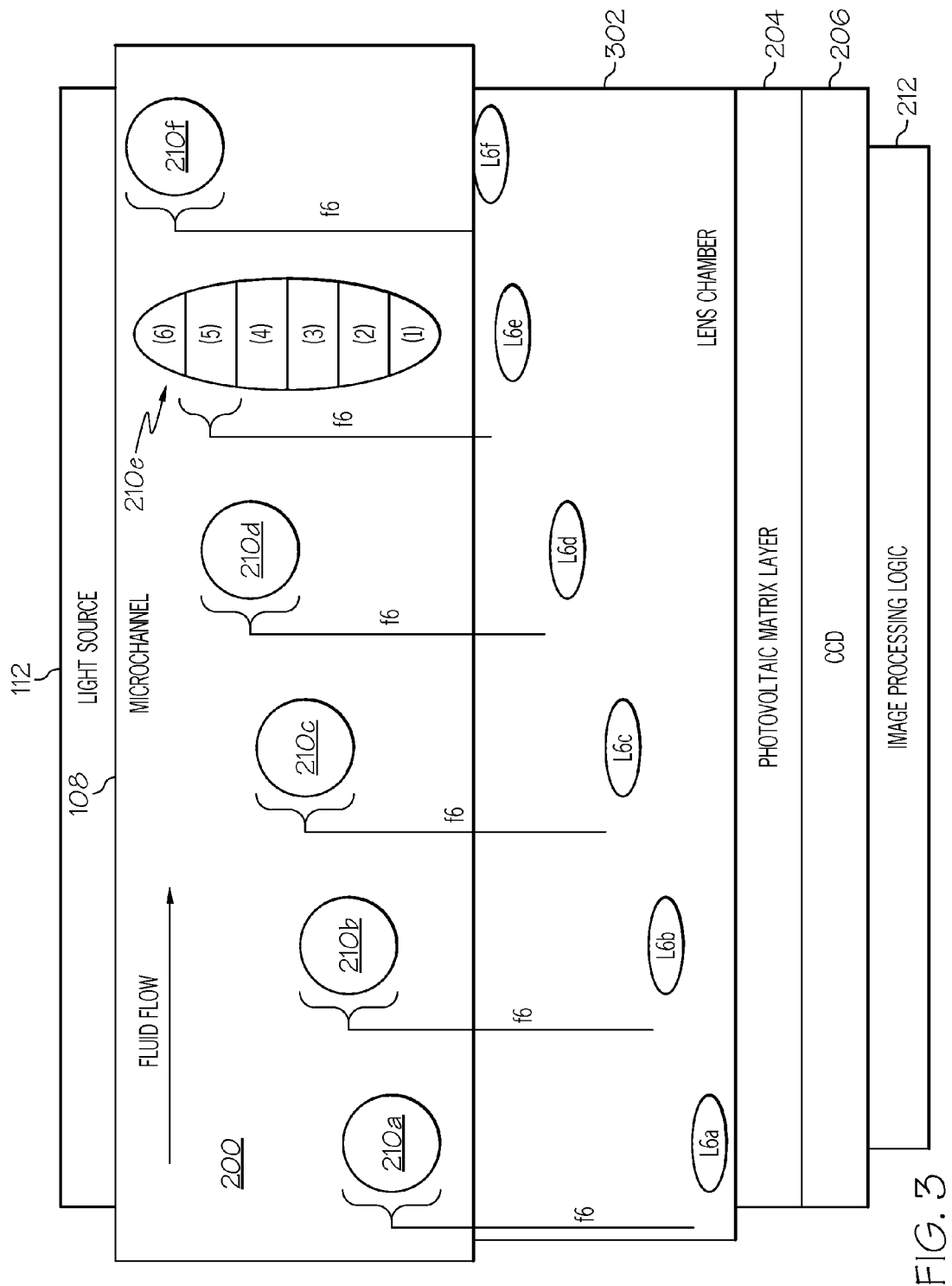
FIG. 3 depicts additional detail of another embodiment of the optic module depicted in FIG. 1.

In one embodiment, a same type/shape of lens is used at all positions, but simply repositioned to create different depths of field to create different effective focal lengths. For example, as shown in FIG. 3, there are six different fixed focus lenses L6a-f. Each of these lenses is identical. However, because they are physically different distances from the microchannel 108, the different fixed focus lenses L6a-f have different effective focal lengths and thus are able to capture crisp images of objects in different longitudinal sections (strata) of the microchannel 108.

Figure 4:
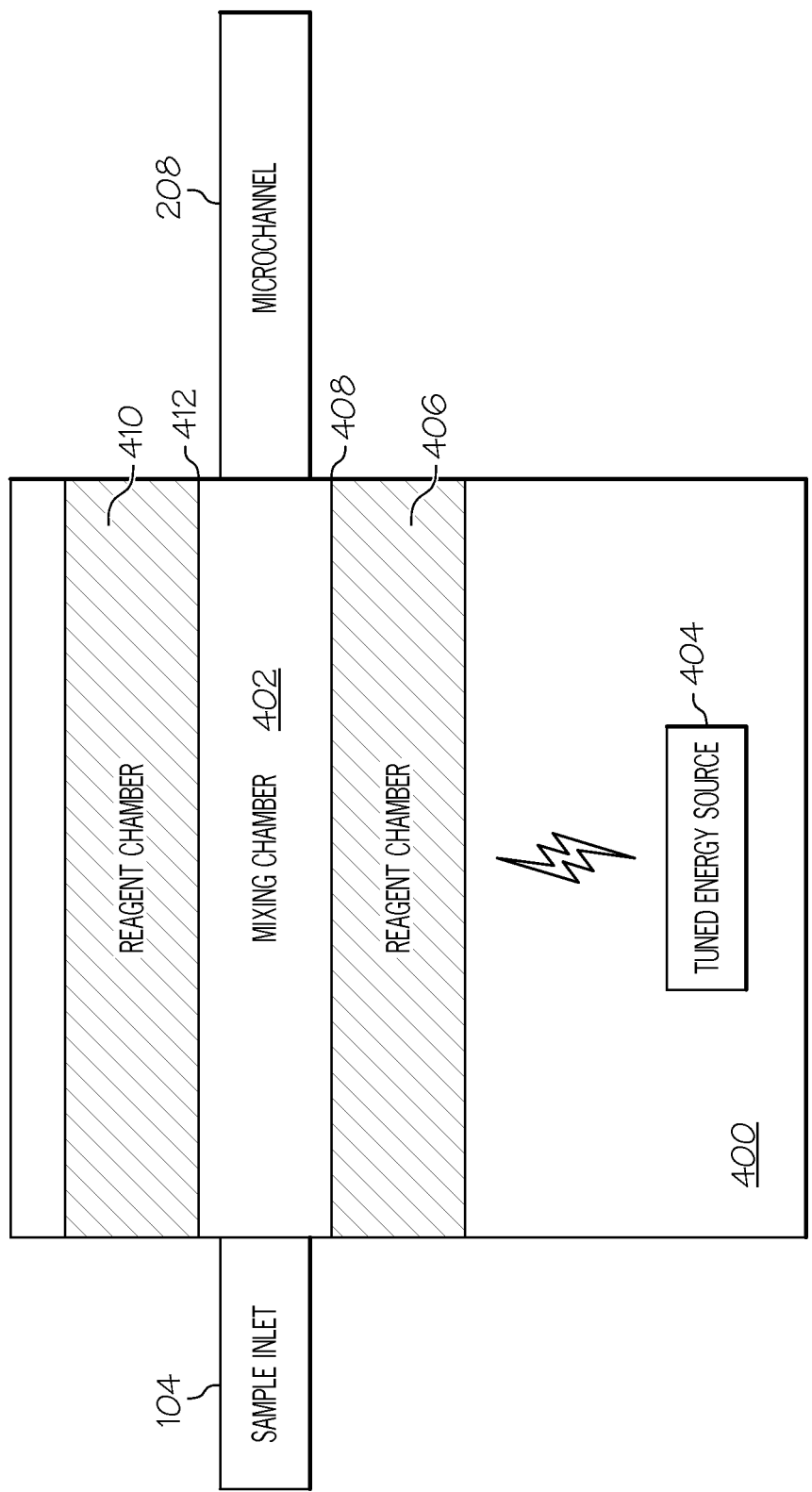
FIG. 4 illustrates additional detail of one embodiment of a sample preparation module depicted in FIG. 1.

With reference now to FIG. 4, additional detail of one embodiment of the SPM 106 shown in FIG. 1 is depicted as SPM 400. Within SPM 400 is a mixing chamber 402. A tuned energy source 404 is able to selectively cause reagents (i.e., chemical reagents, enzymes, coagulators, dyes, etc. needed to prepare objects for viewing within the LOC) to mix with the sample coming in from the sample inlet 104. In one embodiment, this mixing is performed by simply injecting such reagents from a reservoir (not shown) into the mixing chamber 402, and allowing the energy from the tuned energy source 404 (e.g., a laser of a certain frequency/temperature, a resistor or other electronic heating element tuned to a certain temperature, etc.) to cause the materials to mix together due to energy/heat shock.

In one embodiment, the mixing of the reagents is caused by selectively heating pre-loaded (near or at the time of the fabrication of the LOC 102) reagents found in reagent chamber 406 and/or reagent chamber 410. For example, assume that due to its hue, component makeup, etc., a reagent and/or the liquid carrier medium within reagent chamber 406 will heat up if exposed to a certain frequency of light (e.g., a laser) from tuned energy source 404, while this same frequency of light causes the reagent/carrier medium within reagent chamber 410 to remain cool and quiescent. In this example, the reagent within reagent chamber 406 will be forced across semi-permeable membrane 408 due to heat-induced expansion, while the reagent within reagent chamber 410 will remain contained within reagent chamber 410 by semi-permeable membrane 412. Alternatively, reagents from both reagent chambers 406 and 410 may be released into mixing chamber 402 if they are excited by one or more frequencies of laser energy that cause them to expand and traverse across their respective semi-permeable membranes.

Logic within the LOC (e.g., the control unit 118 of the LOC 102 as shown in FIG. 1) may execute code that controls which reagent chambers release their respective reagents into the mixing chamber 402. If there are three reagent chambers that respectively hold reagents A, B, and C for use in creating a mixture/preparation D, then an example of such code is found in the following pseudo code:

```
If test = 1
    then use reagent A
    else if test = 2
        then use reagent A and reagent B simultaneously
        else if test =3
            then use reagent A and reagent C;
    wait 10;
    use preparation D of sample and applied reagents and mix until
    temperature goes up 10 degrees
        else if etc.
```

Figure 5:
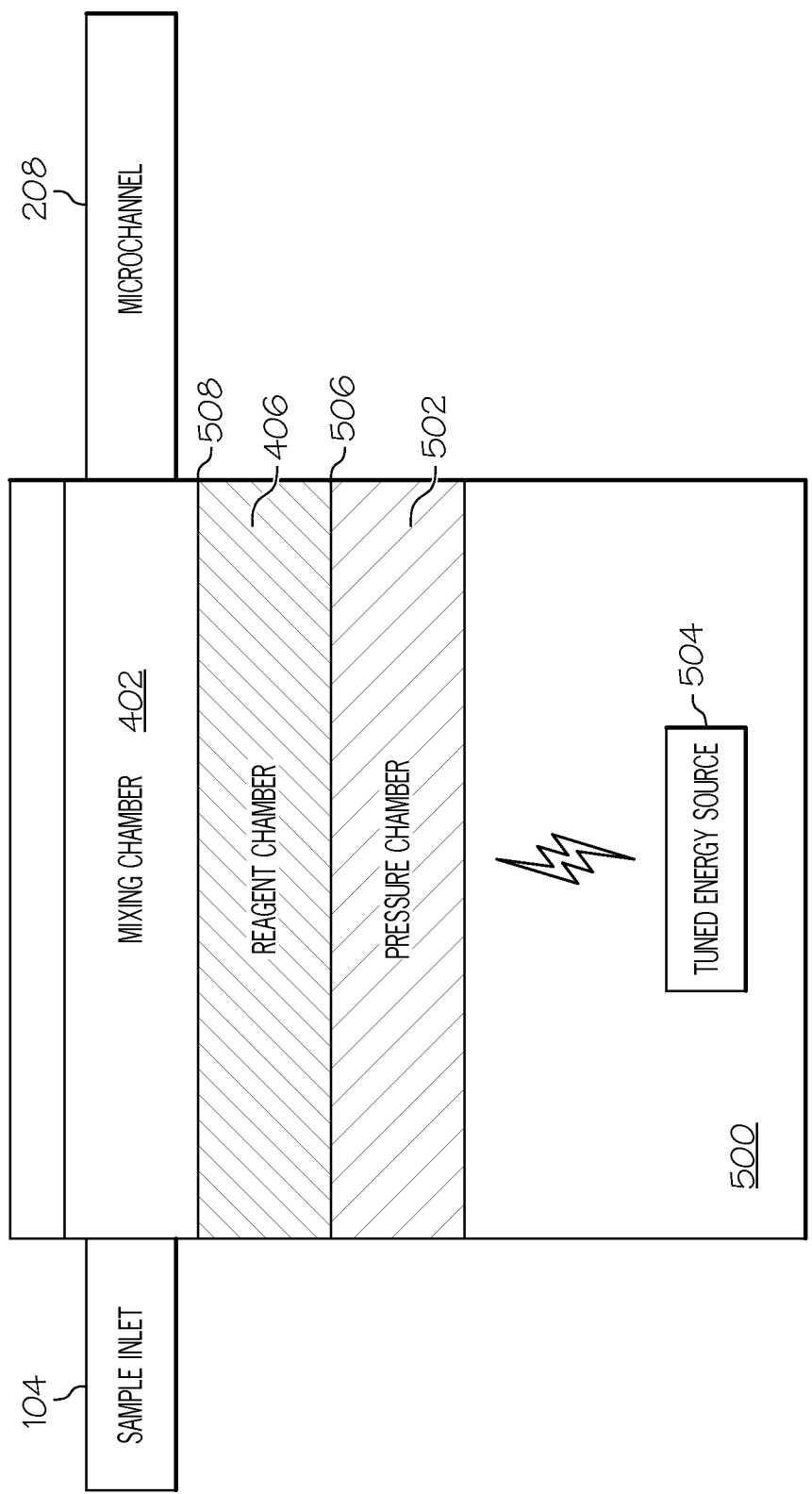
FIG. 5 illustrates additional detail of another embodiment of the sample preparation module depicted in FIG. 1.
Figure 6:
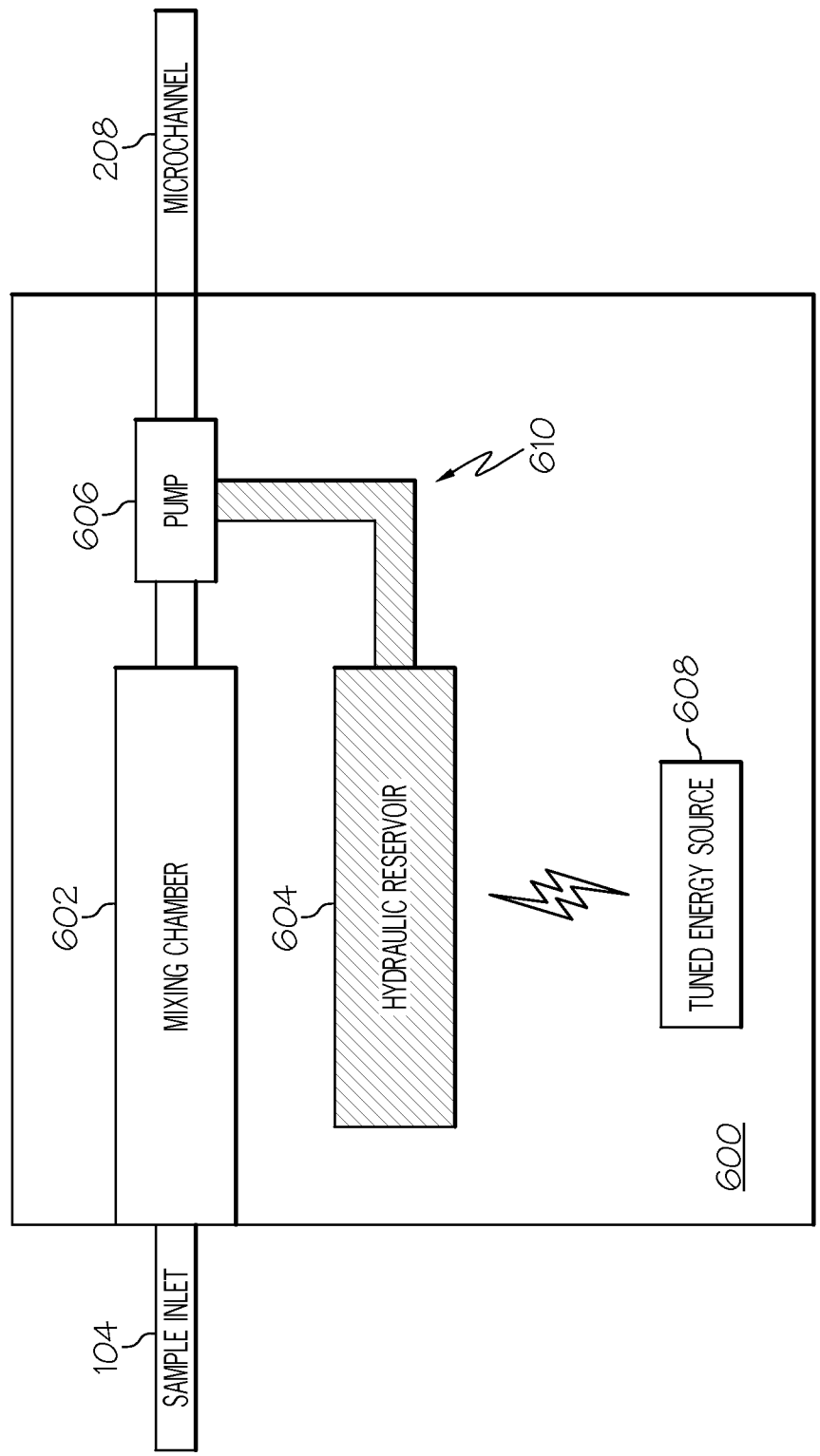
FIG. 6 illustrates additional detail of another embodiment of the sample preparation module depicted in FIG. 1.

In some cases, the reagent within a reagent chamber may be susceptible to damage if overheated. In this case, a pressure chamber can be used. As depicted in FIG. 5, SPM 500 may include a pressure chamber 502, which holds only non-reagent material that nonetheless will expand if exposed to a certain level of heat, frequency of light, etc. from the tuned energy source 504. As such, when energy from the tuned energy source 504 strikes pressure chamber 502, the contents of pressure chamber 502 expand across a semi-permeable membrane 506, forcing the reagent within reagent chamber 406 to be pushed through a semi-permeable membrane 508 and into the mixing chamber 402, while allowing the reagent within reagent chamber 406 to remain cool and otherwise unaffected by the tuned energy source 504. That is, by pre-loading into pressure chamber 502 a fluid that expands at a temperature that is below that which could damage the reagent within reagent chamber 406, then that reagent is unharmed/unaltered. Similarly, by pre-loading into pressure chamber 502 a fluid that expands when exposed to a light frequency that has no adverse effect on the reagent within reagent chamber 406, then that reagent is likewise unharmed/unaltered. Other pressure/reagent chamber pairs (not shown) may selectively introduce other reagents into the mixing chamber 402.

In one embodiment, a tuned heat source can drive a micro-pump, which can be used to 1) mix reagents and/or 2) propel the sample through the SPM 106 shown in FIG. 1. For example, consider SPM 600 shown in FIG. 6. The sample fluid enters a mixing chamber 602 and is prepared as described above. In this example, the tuned energy source 608 causes liquid within hydraulic reservoir 604 to expand, turning an impeller within a miniature pump such as the depicted pump 606. That is, since hydraulic reservoir 604 is fluidly coupled to pump 606 (i.e., fluid from hydraulic reservoir 604 is able to pass through piping 610 from hydraulic reservoir 604 to pump 606), pump 606 is able to pull the sample liquid out of the mixing chamber 602 and push it into the microchannel 208. In one embodiment, the same operation can be used to mix reagents with sample material within the mixing chamber 602 by pumping reagents directly into the mixing chamber 602.

Figure 7:
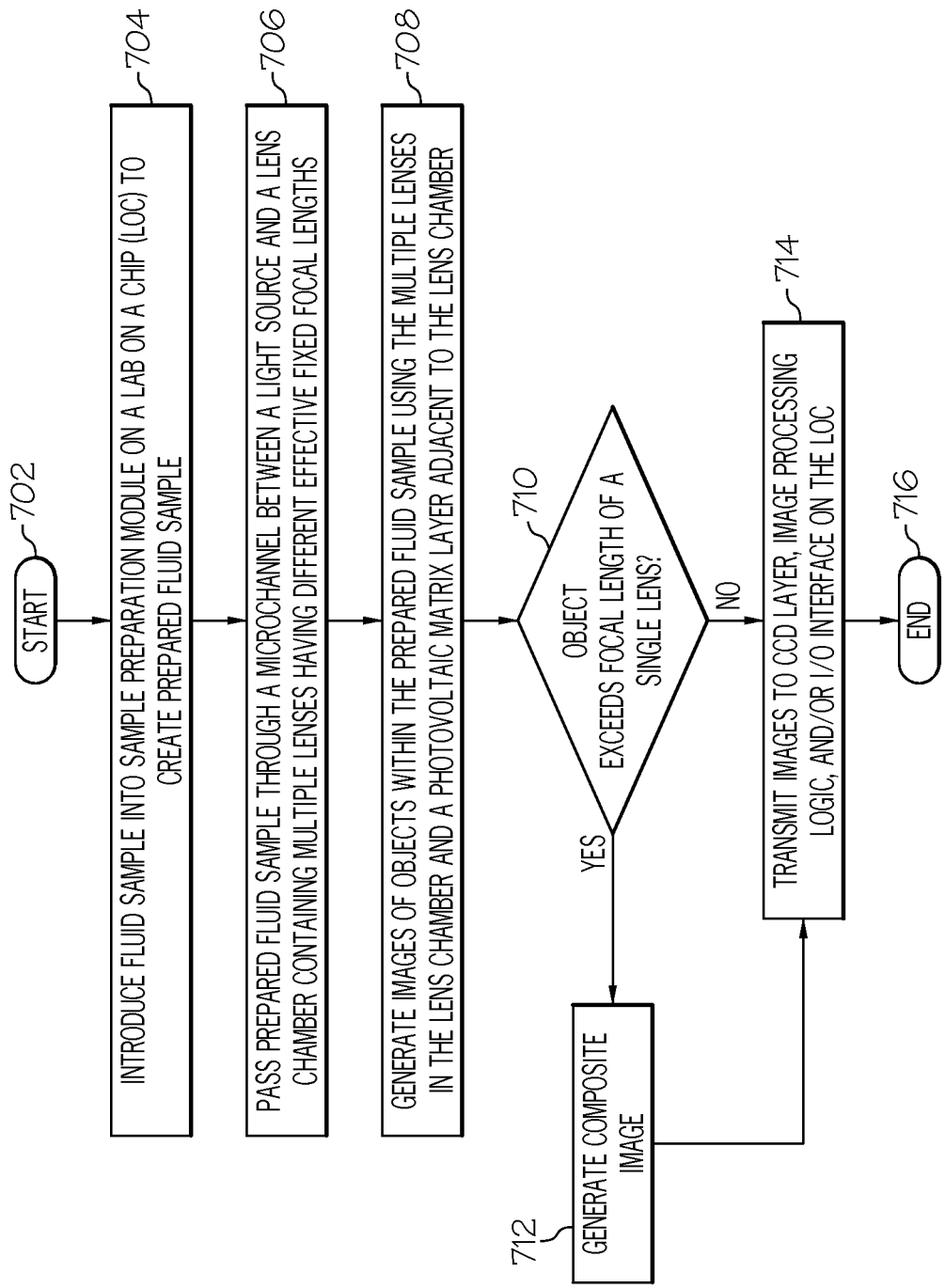
FIG. 7 is a high-level flow chart of one or more steps performed by a processor to analyze a test sample on a LOC.

Referring now to FIG. 7, a high-level flow chart of one or more steps performed by a processor to analyze a test sample on a LOC is presented. After initiator block 702, a fluid sample is introduced into a sample preparation module on a Lab On a Chip (LOC) to create a prepared fluid sample 704. This preparation can be performed through the use of mixing chambers, reagent chambers, pumps, etc. as described above. In one embodiment, this preparation is under the control of a control unit (e.g., control unit 118 shown in FIG. 1), which includes processing logic (e.g., a processor) to control a tuned energy source, pump, etc. shown above.

As described in block 706, the prepared fluid sample is then passed through a microchannel that is positioned near a light source and a lens chamber. The lens chamber holds multiple lenses, each of which have a different effective fixed focal length. That is, each lens may have a shape/composition that causes it to have a different focal length than other lenses within the lens chamber (as depicted in FIG. 2), or duplicate copies of a same lens may be physically repositioned in order to create different effective focal lengths (as depicted in FIG. 3).

As described in block 708, images of passing-by objects within the prepared fluid sample are generated using the multiple lenses in the lens chamber and a photovoltaic matrix layer adjacent to the lens chamber. If any of the objects are larger than the focal length of any one of the multiple fixed-focal length lenses (query block 710), then a composite image of that large object is generated using snapshots from multiple lenses (block 712). Once the image, either singular or composite, is generated by the lens(es) and the photovoltaic matrix layer, the images are transmitted to a CCD layer and an image processing logic to be converted into a digital image. The digital image is then transmitted to an I/O interface on the LOC (block 714) for transmission to a monitor, printer, external computer/server, etc. The process ends at terminator block 716.

Figure 8:
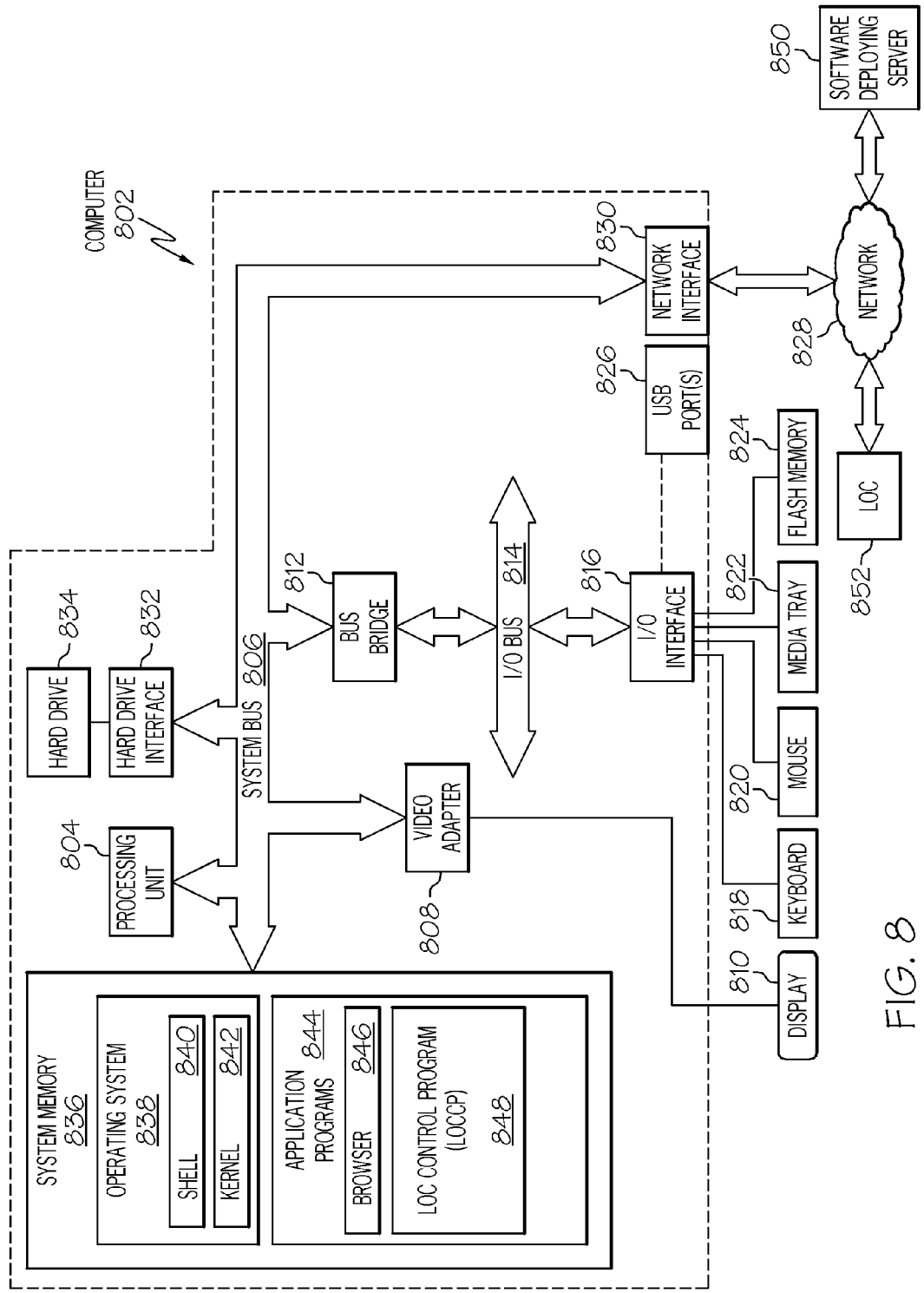
FIG. 8 depicts an exemplary computer system that may be utilized by one or more of the components depicted in FIGS. 1-6.

With reference now to FIG. 8, there is depicted a block diagram of an exemplary computer 802, which may be utilized by the present invention. Note that some or all of the exemplary architecture, including both depicted hardware and software, shown for and within computer 802 may be utilized by software deploying server 850 and/or a Lab On a Chip (LOC) 852. For example, the LOC 852 may utilize a processor such as that found in processing unit 804, a memory such as system memory 836, a flash memory such as flash memory 824 (e.g., an EPROM) to function as the control unit 118 depicted in FIG. 1.

Computer 802 includes a processor 804 that is coupled to a system bus 806. Processor 804 may utilize one or more processors, each of which has one or more processor cores. A video adapter 808, which drives/supports a display 810, is also coupled to system bus 806. System bus 806 is coupled via a bus bridge 812 to an input/output (I/O) bus 814. An I/O interface 816 is coupled to I/O bus 814. I/O interface 816 affords communication with various I/O devices, including a keyboard 818, a mouse 820, a media tray 822 (which may include storage devices such as CD-ROM drives, multi-media interfaces, etc.), a flash memory 824 (e.g., a flash drive, an Erasable Programmable Read Only Memory—EPROM, a Read Only Memory (ROM), etc.), and external USB port(s) 826. While the format of the ports connected to I/O interface 816 may be any known to those skilled in the art of computer architecture, in one embodiment some or all of these ports are universal serial bus (USB) ports.

As depicted, computer 802 is able to communicate with a software deploying server 850 and/or a LOC 852 using a network interface 830 to a network 828. Network 828 may be an external network such as the Internet, or an internal network such as an Ethernet or a virtual private network (VPN).

A hard drive interface 832 is also coupled to system bus 806. Hard drive interface 832 interfaces with a hard drive 834. In one embodiment, hard drive 834 populates a system memory 836, which is also coupled to system bus 806. System memory is defined as a lowest level of volatile memory in computer 802. This volatile memory includes additional higher levels of volatile memory (not shown), including, but not limited to, cache memory, registers and buffers. Data that populates system memory 836 includes computer 802's operating system (OS) 838 and application programs 844.

OS 838 includes a shell 840, for providing transparent user access to resources such as application programs 844. Generally, shell 840 is a program that provides an interpreter and an interface between the user and the operating system. More specifically, shell 840 executes commands that are entered into a command line user interface or from a file. Thus, shell 840, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 842) for processing. Note that while shell 840 is a text-based, line-oriented user interface, the present invention will equally well support other user interface modes, such as graphical, voice, gestural, etc.

As depicted, OS 838 also includes kernel 842, which includes lower levels of functionality for OS 838, including providing essential services required by other parts of OS 838 and application programs 844, including memory management, process and task management, disk management, and mouse and keyboard management.

Application programs 844 include a renderer, shown in exemplary manner as a browser 846. Browser 846 includes program modules and instructions enabling a world wide web (WWW) client (i.e., computer 802) to send and receive network messages to the Internet using hypertext transfer protocol (HTTP) messaging, thus enabling communication with software deploying server 850 and other described computer systems.

Application programs 844 in computer 802's system memory (as well as software deploying server 850's system memory) also include a Lab On a Chip Control Program (LOCCP) 848. LOCCP 848 includes code for implementing the processes described below, including those described in FIGS. 1-7. In one embodiment, computer 802 is able to download LOCCP 848 from software deploying server 850, including in an on-demand basis, wherein the code in LOCCP 848 is not downloaded until needed for execution to define and/or implement the improved enterprise architecture described herein. Note further that, in one embodiment of the present invention, software deploying server 850 performs all of the functions associated with the present invention (including execution of LOCCP 848), thus freeing computer 802 from having to use its own internal computing resources to execute LOCCP 848.

The hardware elements depicted in computer 802 are not intended to be exhaustive, but rather are representative to highlight essential components required by the present invention. For instance, computer 802 may include alternate memory storage devices such as magnetic cassettes, digital versatile disks (DVDs), Bernoulli cartridges, and the like. These and other variations are intended to be within the spirit and scope of the present invention.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:
1. A Lab On a Chip (LOC) comprising:
  a sample inlet for receiving a liquid sample;
  a Sample Preparation Module (SPM) coupled to the sample inlet, wherein the SPM comprises:
  a mixing chamber;
  a reagent chamber containing a reagent;
  a first semi-permeable membrane oriented between the mixing chamber and the reagent chamber;
  a pressure chamber containing a non-reagent fluid;
  a second semi-permeable membrane oriented between the pressure chamber and the reagent chamber; and
  a tuned energy source, wherein the tuned energy source selectively causes the non-reagent fluid in the pressure chamber to expand and pass through the second semi-permeable membrane to pressurize contents of the reagent chamber, and wherein pressurizing the contents of the reagent chamber forces the reagent across the first semi-permeable membrane in order to mix the reagent with the liquid sample;
  a microchannel coupled to the SPM;
  a light source;
  an optic module optically proximate to the microchannel;
  a plurality of lenses within the optic module, wherein each of the plurality of lenses has a different effective focal length for focusing light images of objects suspended within the liquid sample as light from the light source illuminates the objects passing through the microchannel in different strata of the microchannel; and an image processing component within the optic module, wherein the image processing component generates a digital image of the light images of the objects.

2. The LOC of claim 1, wherein different effective focal lengths are achieved by each of the plurality of lenses being manufactured of different materials having different indexes of refraction.

3. The LOC of claim 1, further comprising:
an effluent reservoir fluidly coupled to the microchannel, wherein the effluent reservoir captures the liquid sample as it leaves the microchannel.

4. The LOC of claim 1, wherein a single object within the microchannel extends across multiple focal lengths of lenses from the plurality of lenses, wherein the plurality of lenses focus on the different strata of the microchannel to create multiple snapshots of different regions of the single object, and wherein the optic module combines the multiple snapshots taken at the multiple focal lengths into a single composite image of the single object.

5. The LOC of claim 1, further comprising:
a control unit, wherein the control unit controls a timing at which images of multiple objects suspended in the liquid sample in the microchannel are captured using the plurality of lenses, wherein the control unit derives the timing by controlling a flow rate of the liquid sample through the microchannel to 1) ensure that each of multiple objects in the liquid sample is in focus at a point in time at which each object is adjacent to one of the multiple lenses, and to 2) avoid counting a same object in the liquid sample twice.

6. A Lab On a Chip (LOC) comprising:
a sample inlet for receiving a liquid sample;
a Sample Preparation Module (SPM) coupled to the sample inlet, wherein the SPM comprises:
a mixing chamber;
a reagent chamber containing a reagent;
a semi-permeable membrane oriented between the mixing chamber and the reagent chamber; and
a tuned energy source, wherein the tuned energy source selectively causes contents of the reagent chamber to expand and pass through the semi-permeable membrane into the mixing chamber to mix the reagent with the liquid sample;
a microchannel coupled to the SPM;
a light source;
an optic module optically proximate to the microchannel;
a plurality of lenses within the optic module, wherein each of the plurality of lenses has a different effective focal length for focusing light images of objects suspended within the liquid sample as light from the light source illuminates the objects passing through the microchannel in different strata of the microchannel; and
an image processing component within the optic module, wherein the image processing component generates a digital image of the light images of the objects.

7. The LOC of claim 6, wherein different effective focal lengths are achieved by each of the plurality of lenses being manufactured of different materials having different indexes of refraction.

8. The LOC of claim 6, further comprising:
an effluent reservoir fluidly coupled to the microchannel, wherein the effluent reservoir captures the liquid sample as it leaves the microchannel.

9. The LOC of claim 6, wherein a single object within the microchannel extends across multiple focal lengths of lenses from the plurality of lenses, wherein the plurality of lenses focus on the different strata of the microchannel to create multiple snapshots of different regions of the single object, and wherein the optic module combines the multiple snapshots taken at the multiple focal lengths into a single composite image of the single object.

10. The LOC of claim 6, further comprising:
a control unit, wherein the control unit controls a timing at which images of multiple objects suspended in the liquid sample in the microchannel are captured using the plurality of lenses, wherein the control unit derives the timing by controlling a flow rate of the liquid sample through the microchannel to 1) ensure that each of multiple objects in the liquid sample is in focus at a point in time at which each object is adjacent to one of the multiple lenses, and to 2) avoid counting a same object in the liquid sample twice.

* * * * *